US012570721B2

(12) United States Patent
Bataille et al.

(10) Patent No.: US 12,570,721 B2
(45) Date of Patent: Mar. 10, 2026

(54) METHOD FOR FILTERING FIBRINOGEN

(71) Applicant: Laboratoire Francais du Fractionnement et des Biotechnologies, Les Ulis (FR)

(72) Inventors: Damien Bataille, Ormoy (FR); Monique Ollivier, Le Kremlin Bicetre (FR); Michel Tellier, Eaubonne (FR)

( * ) Notice: Subject to any disclaimer, the term of this patent is extended or adjusted under 35 U.S.C. 154(b) by 833 days.

(21) Appl. No.: 17/416,143

(22) PCT Filed: Dec. 20, 2019

(86) PCT No.: PCT/FR2019/053235
§ 371 (c)(1),
(2) Date: Jun. 18, 2021

(87) PCT Pub. No.: WO2020/128385
PCT Pub. Date: Jun. 25, 2020

(65) Prior Publication Data
US 2022/0056107 A1      Feb. 24, 2022

(30) Foreign Application Priority Data
Dec. 21, 2018    (FR) ...................................... 1873741

(51) Int. Cl.
| | |
|---|---|
| *C07K 14/75* | (2006.01) |
| *C07K 1/18* | (2006.01) |
| *C07K 1/34* | (2006.01) |

(52) U.S. Cl.
CPC ................ *C07K 14/75* (2013.01); *C07K 1/18* (2013.01); *C07K 1/34* (2013.01)

(58) Field of Classification Search
CPC ............. C07K 14/15; C07K 1/18; C07K 1/34
See application file for complete search history.

(56) References Cited

U.S. PATENT DOCUMENTS

| | | | |
|---|---|---|---|
| 2003/0232969 A1 | 12/2003 | Lengsfeld et al. | |
| 2011/0114524 A1 | 5/2011 | Eibl | |
| 2017/0073396 A1* | 3/2017 | Bataille ................. | A61K 38/38 |
| 2019/0016755 A1 | 1/2019 | Schulz et al. | |

FOREIGN PATENT DOCUMENTS

| | | | |
|---|---|---|---|
| EP | 1457497 | 9/2004 | |
| WO | 2013062305 A1 | 5/2013 | |
| WO | 2014085861 | 6/2014 | |
| WO | WO-2015017888 A1* | 2/2015 ............... | A61P 3/06 |

OTHER PUBLICATIONS

Husain, et al., "Interaction of Fibrinogen and Its Derivatives with Fibrin." JBC, 264; 19: 11414-11420. (Year: 1989).*
Caballero et al., "Robustness of nanofiltration for increasing the viral safety margin of biological products," Biologicals, vol. 42, pp. 79-85, Jan. 2014.
International Search Report issued in application No. PCT/FR2019/053235 dated Mar. 17, 2020.
Amendment after final filed in Pham et al., U.S. Appl. No. 17/188,173, Oct. 24, 2023.
Response filed in Pham et al., U.S. Appl. No. 17/188,173, Jan. 17, 2024.

* cited by examiner

*Primary Examiner* — Suzanne M Noakes
*Assistant Examiner* — Ciara A McKnight
(74) *Attorney, Agent, or Firm* — Rouget F. Henschel; Potomac Law Group, PLLC

(57) ABSTRACT

Disclosed is a method for filtering a fibrinogen composition, including the following steps: a) purifying the fibrinogen composition by chromatographic purification using an elution buffer comprising arginine; b) optionally, at least one step of filtering the fibrinogen composition obtained by chromatographic elution in step a), on a filter having a pore size of between 0.08 μm and 0.22 μm, c) filtering the fibrinogen composition obtained by chromatographic elution in step a), or optionally obtained in step b), on a symmetrical filter having a pore size of between 15 nm and 25 nm, and preferably between 18 nm and 22 nm, and d) recovering the resulting fibrinogen solution, the filtering method being carried out without adding arginine after step a), at a high capacity and without a prior freezing and/or thawing step.

16 Claims, 1 Drawing Sheet

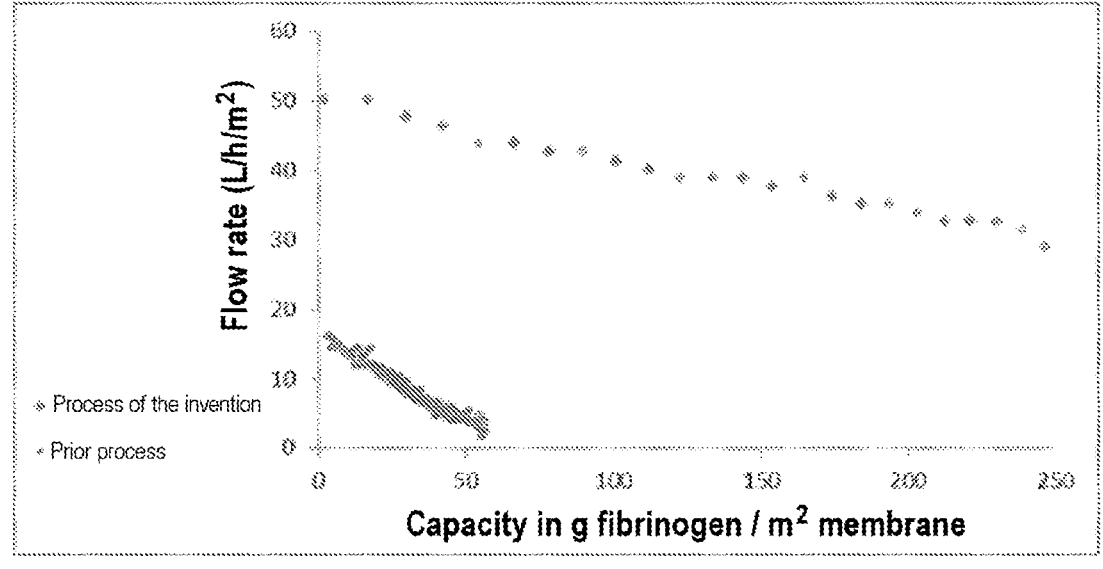

METHOD FOR FILTERING FIBRINOGEN

TECHNICAL FIELD

The present invention relates to a process for filtering fibrinogen and to the preparations obtained.

PRIOR ART

Fibrinogen is an essential blood coagulation protein because its polymerization into insoluble fibrin, formed at the end of the cascade of reactions that govern coagulation, leads to the formation of a clot that blocks the vascular breach responsible for the bleeding. Clot establishment is thus essential to ensure that bleeding is stopped. In addition, fibrin formed in the wound constitutes a fibrillar network that ensures tissue repair and, therefore, healing.

Congenital fibrinogen deficiencies can lead to serious pathologies. To treat these deficiencies, it is necessary to have fibrinogen concentrates that can be administered to patients. Other pathologies can also be treated by providing fibrinogen, in particular in cases of massive blood loss, for example in cases of surgery or trauma, or following a decompensated consumption coagulopathy, for example disseminated intravascular coagulation (DIC).

Consequently, the provision of compositions comprising fibrinogen, in particular for therapeutic purposes, requires purification techniques that lead to a product which is not only sufficiently purified from contaminants of various kinds, such as accompanying or co-purified proteins, antibodies or proteases, but also safe in terms of viruses and of non-conventional transmissible agents covering prions.

The isolation of fibrinogen-enriched fractions from plasma is known and was first described by the work of Cohn and Nitschmann (Cohn et al., J. Am. Chem. Soc., 68, 459, 1946 and Kistler et al., Vox Sang., 7, 1962, 414-424). More recent methods incorporate preparation techniques by precipitation, chromatography with dedicated biosafety steps.

In particular, certain conventional viral inactivation treatments consist of heat treatment, for example pasteurization at 60° C. for 20 h in the presence of protective stabilizers or dry heating of the freeze-dried product, and/or chemical treatment, such as by solvent-detergent, which are intended to make the fibrinogen compositions compatible with a therapeutic use. However, they do not make it possible to ensure total inactivation of viruses, in particular non-enveloped viruses such as parvovirus B19 or hepatitis A or B virus, without impacting the protein. In particular, if these treatments are not perfectly controlled, they can lead to degradation of the protein (loss of biological activity, denaturation by enzymatic action) and the formation of fragments, aggregates and polymers.

Other biosafety methods use viral removal techniques, particularly using filtrations. Nevertheless, these filtration techniques require filters of small pore size (<35 nanometers) that are relatively incompatible with fibrinogen. The application EP1457497 describes a nanofiltration step requiring a preliminary freezing and thawing step followed by filtration that must be applied in order to remove aggregates, polymers or undesirable contaminants such as fibronectin; such a process also requires a prior dilution of the solution to less than 2 g/L to limit premature clogging of the filters, which represents a significant impediment to the industrialization of such processes. Thus, low-porosity filters such as the PLANOVA™ 20N filter, which is conventionally used in the industry for biosafety, do not make it possible to reach a load on the filter that is sufficient to ensure an acceptable industrial cost price yield. Processes using filters under such conditions do not allow easy industrial implementation or high capacity use and represent a prohibitive cost in the implementation of an industrial scale purification process using starting batches of several hundreds or thousands of liters.

In particular, such processes do not allow treatment of more than 0.2 kg of fibrinogen per $m^2$ of nanofilter membrane without including a preliminary step of freezing/thawing and filtration of the product to be nanofiltered. For the person skilled in the art, the development of a fibrinogen nanofiltration step under conditions allowing its industrial implementation (sufficient flow rate, little clogging, acceptable cost price) is therefore known to be a challenge.

Furthermore, it is known to the skilled person that fibrinogen compositions must contain arginine to ensure their stability. Thus, processes for obtaining fibrinogen compositions use arginine in various steps of the process, including during elution chromatography. However, the application US2015/0366947 (example 7) teaches that nanofiltration of fibrinogen compositions obtained by elution chromatography in buffer comprising arginine would not be made easier compared with nanofiltration of fibrinogen compositions obtained by elution chromatography in buffer not comprising arginine. Indeed, according to this process, the use of an elution chromatography buffer comprising arginine leads to clogging of the filter and requires the addition of an adjustment step with arginine of the composition obtained after the chromatography step, in order to overcome the impossibility of nanofiltering the composition. Therefore, a process that is simpler to implement would have an advantage.

Technical Problem

The applicant has therefore sought to develop a process for removing viruses and other undesirable contaminants (such as polymers, aggregates or prions) from a composition comprising fibrinogen, by filtration, which makes it possible to obtain a highly safe fibrinogen composition, said process being easy to implement on an industrial scale and having a good yield and an acceptable industrial cost price.*

Disclosure of the Invention

The invention therefore relates to a process for filtering a fibrinogen composition, comprising the following steps:
  a) chromatographic purification of the fibrinogen composition using an elution buffer comprising arginine;
  b) optionally, at least one step of filtering the fibrinogen composition obtained by elution chromatography in step a), on a filter having a pore size comprised between 0.08 μm and 0.22 μm,
  c) filtering the fibrinogen composition obtained by elution chromatography in step a) or optionally obtained in b), on a symmetrical filter having a pore size comprised between 15 nm and 25 nm, preferably comprised between 18 nm and 22 nm, and
  d) recovering the resulting fibrinogen solution,
  said filtration process being carried out without addition of arginine after step a), at a capacity of at least 0.2 kg fibrinogen/$m^2$ and said fibrinogen composition not being previously frozen and/or thawed.

Such a solution makes it possible to solve the problems posed by the known prior art solutions and in particular allows a highly biologically safe solution to be obtained at the end of step d).

Indeed, and advantageously, the process in accordance with the invention does not require the addition of a step of adjustment with arginine of the composition obtained after the chromatography step. It has indeed been shown that increasing concentrations of arginine in the elution buffer make it possible to increase the filtration capacity and do not lead to clogging of the filter. A subsequent adjustment step with arginine is therefore unnecessary, thus simplifying the industrial implementation of the process.

The process in accordance with the invention thus advantageously allows the filterability, on a symmetrical filter with a pore size of about 20 nm, of a composition comprising fibrinogen without a prior freezing/thawing step, nor prior dilution from a solution of fibrinogen prepurified by chromatography, eluted by a buffer comprising arginine, and without addition of arginine after the chromatographic purification step.

BRIEF DESCRIPTION OF THE DRAWINGS

Other features, details and advantages of the invention will become apparent upon reading the following detailed description and analyzing the appended drawings, in which:

FIG. 1

FIG. 1 shows the capacity in g fibrinogen/$m^2$ membrane as a function of the flow rate (L/H/$m^2$) of the process in accordance with the invention (symmetrical filter) compared with a prior process (asymmetrical filter)

DESCRIPTION OF THE EMBODIMENTS

The following drawings and description below essentially contain elements of a certain nature. Therefore, they may not only serve to better elucidate the present invention, but also contribute to its definition, if need be.

In the present application, "high capacity" means a fibrinogen load per membrane area, expressed as kg fibrinogen per $m^2$ membrane, greater than or equal to 0.2, preferably greater than or equal to 0.25, preferably greater than or equal to 0.3, preferably greater than or equal to 0.35, preferably greater than or equal to 0.4, preferably greater than or equal to 0.45, preferably greater than or equal to 0.5, preferably greater than or equal to 1, preferably greater than or equal to 2, preferably greater than or equal to 3, preferably greater than or equal to 5 kg/$m^2$.

Particularly advantageously, the high capacity corresponds to a fibrinogen load per membrane area comprised between 0.2 and 5 kg/$m^2$, even more advantageously between 0.2 and 2.5 kg/$m^2$.

Thus, the applicant has found that it is possible to obtain, on an industrial scale, highly safe fibrinogen compositions, free of viruses, and in particular of small viruses, in particular non-enveloped viruses, such as B19, and other undesirable contaminants (such as polymers, aggregates or prions), by implementing a flexible and simple filtration process that enables safety of the fibrinogen with a nanofiltration step which preserves its molecular integrity at an acceptable production cost. Such a simple and rapid process, which has an industrially acceptable cost price is easily implemented on an industrial scale, which leads to an increased optimization of the biosafety of compositions comprising fibrinogen. Finally, such a filtration process allows a high protein load with a high yield after filtration.

In addition, such a process is optimal, because it does not require in particular:

prior freezing/thawing steps intended to remove undesirable aggregates or contaminants, and/or prior dilution steps, which decrease protein concentration and extend filtration times, and/or arginine removal steps in the preceding purification steps, which makes it possible to keep a fibrinogen stabilized and/or a step of adjustment with arginine of the composition obtained after the chromatographic purification step carried out using an elution buffer comprising arginine.

In accordance with the invention, more than one source of fibrinogen-containing raw material may be used. The process in accordance with the invention thus uses a fibrinogen composition, in particular from different sources. The fibrinogen composition may thus be derived from blood plasma, preferably from plasma fractions, from cell culture supernatant or from milk of transgenic animals.

In a particular embodiment, the fibrinogen-comprising composition (or fibrinogen composition) subjected to the process of the invention is blood plasma or a plasma fraction, preferably a plasma fraction obtained from prepurified blood plasma.

"Plasma fraction obtained from prepurified blood plasma" means any part or subpart of human blood plasma that has undergone one or more purification steps. Said plasma fractions thus include cryoprecipitated plasma supernatant, cryoprecipitated plasma (resuspended), fraction I obtained by ethanol fractionation (according to the Cohn or the Kistler & Nitschmann method), chromatography eluates and non-adsorbed fractions from chromatography columns, including multicolumn chromatography, and filtrates.

In an embodiment of the invention, the fibrinogen composition subjected to the process of the invention undergoes an additional chromatography step. Thus, according to an embodiment, the fibrinogen composition subjected to the process in accordance with the invention is a chromatography eluate or a non-adsorbed fraction from a chromatography column, including multicolumn chromatography.

Thus, in a preferred embodiment of the invention, the fibrinogen composition subjected to the process of the invention is a plasma fraction obtained from cryosupernatant or resuspended cryoprecipitate.

In accordance with the invention, "cryoprecipitated plasma supernatant", or "cryosupernatant", corresponds to the liquid phase obtained after thawing of frozen plasma (cryoprecipitation). In particular, the cryosupernatant can be obtained by freezing blood plasma at a temperature comprised between $-10°$ C. and $-40°$ C., then gently thawing at a temperature comprised between $0°$ C. and $+6°$ C., preferentially between $0°$ C. and $+1°$ C., followed by centrifugation of the thawed plasma to separate the cryoprecipitate and the cryosupernatant. The cryoprecipitate is a concentrate of fibrinogen, fibronectin, von Willebrand factor and factor VIII, while the cryosupernatant contains complement factors, vitamin K dependent factors such as protein C, protein S, protein Z, factor II, factor VII, factor IX and factor X, fibrinogen, immunoglobulins and albumin.

"Fibrinogen composition not being previously frozen and/or thawed" is understood to mean that the fibrinogen composition which is subjected to step b) if applicable, or by default subjected directly to step c), is not frozen and/or thawed prior to this step b) or c).

In an advantageous embodiment of the invention, the plasma fraction subjected to the process of the invention can be obtained according to the process described by the applicant in the application EP1739093. According to this embodiment, the plasma fraction used is preferably obtained as follows:

Human plasma cryosupernatant is preferably used. This plasma cryosupernatant is subjected to ethanol precipitation by the Cohn process, according to conditions known to the person skilled in the art, in particular such that the concentration of ethanol in the plasma under consideration is from 8% to 10% (v/v).

The supernatant and the precipitate thus obtained are then centrifuged. The precipitate constitutes Cohn fraction I composed predominantly of fibrinogen (purity about 70%).

This prepurified Cohn fraction I is resuspended and washed by dispersion.

After centrifugation, the purified precipitate paste (purified Cohn fraction I) is recovered and solubilized.

The solution thus obtained is then subjected to a removal of procoagulant factors by alumina gel treatment at pH 6.9-7.1.

After filtration, this prepurified solution is subjected to a first viral inactivation treatment by solvent-detergent in the presence of Tween®-TnBP.

The prepurified solution thus obtained is injected onto a chromatographic column filled with a DEAE Macro-Prep anion-exchange gel (commercialized by the company BIO-RAD, France), previously equilibrated with a buffer consisting of sodium chloride and trisodium citrate, adjusted to a pH of 8.0.

The elution of fibrinogen is carried out by a suitable elution buffer, for example containing 1 M sodium chloride and a mixture consisting of trisodium citrate, lysine, glycine, arginine and isoleucine, adjusted to pH 7.5.

The eluate thus recovered constitutes the plasma fraction used for the nanofiltration. In the process in accordance with the invention, the chromatography step is performed by affinity, mixed-mode or ion-exchange chromatography.

In a particular embodiment, the chromatographic purification is ion-exchange chromatography. Preferably, it is performed on an ion-exchange matrix based on a natural or synthetic polymer, resin or gel, on which weak base-type anion-exchange groups, preferably DEAE, are grafted. Preferably, the chromatographic purification comprises a first step of loading a fibrinogen composition, in particular the solubilized plasma fraction, onto a weak base-type anion exchanger, said exchanger being previously equilibrated with a buffer of predetermined ionic strength of basic pH. Said buffer is called equilibration buffer.

In the process in accordance with the invention, the elution buffer comprises arginine in arginine is preferentially at least 200 mM, at least 300 mM, at least 400 mM, at least 500 mM, at least 600 mM, at least 700 mM, at least 800 mM, at least 900 mM, at least 1 M.

In a preferred embodiment, the arginine concentration of the elution buffer is preferentially comprised between 200 and 800 mM, between 200 and 700 mM, between 200 and 600 mM, between 200 and 500 mM, between 200 and 400 mM, between 200 and 300 mM.

In another embodiment, the arginine concentration of the elution buffer is preferentially comprised between 300 and 800 mM, between 400 and 800 mM, between 500 and 800 mM, between 600 and 800 mM, between 700 and 800 mM.

In another embodiment, the arginine concentration of the elution buffer is preferentially comprised between 300 and 800 mM, between 400 and 700 mM, between 400 and 600 mM.

In the process in accordance with the invention, the elution buffer may also contain other suitable excipients, such as salts and/or amino acids, for example trisodium citrate, Tris, lysine, glycine, and/or isoleucine. The protein concentration in the eluate is of the order of 2 to 5 g/L.

In a particular embodiment, the chromatographic purification is affinity chromatography. Preferably, the chromatographic purification comprises a first step of loading a fibrinogen composition, derived from the cryosupernatant or resuspended cryoprecipitate, onto an affinity resin, said resin being previously equilibrated with a buffer of predetermined ionic strength of suitable pH. Said buffer is called equilibration buffer.

Thus, preferably, during step a), the solubilized plasma fraction is loaded onto any affinity matrix, resin or gel, on which are grafted chemical or synthetic ligands such as antibodies, antibody fragments, antibody derivatives or chemical ligands such as peptides, peptide mimetics, peptoids, nanofitins or oligonucleotide ligands such as aptamers. In a particular embodiment, the chromatographic support is available under the name CAPTURESELECT™ Fibrinogen (commercialized by the company LIFE TECHNOLOGIES). In another particular embodiment, the chromatographic support is obtained according to the method described in the application WO2018007530.

In an advantageous embodiment of the invention, the plasma fraction subjected to the process of the invention can thus be obtained according to the process described by the applicant in the application WO2015/136217 or in the application WO2018007530.

Advantageously, the affinity chromatography can be performed in continuous chromatography of the simulated moving bed (SMB) type, for example with NOVASEP company sequential multicolumn chromatography (SMCC) technology. By using between 2 and 8 small columns performing several purification cycles in order to purify all the fibrinogen, the size of the columns and the chromatography equipment is reduced significantly (by a factor of about 10). Moreover, by overloading the affinity resin during the fibrinogen load phases, the resin requirement per fibrinogen batch can be reduced by 10% to 50% in general. The eluates generated in continuous chromatography can either be used continuously for the following steps with or without on-line concentration using on-line concentration equipment of the Pall® Cadence™ type or equivalent from other suppliers. An alternative consists in pooling the eluates before continuing the process, with possible reconcentration of the eluates before use thereof.

In an advantageous embodiment of the invention, the affinity chromatography is performed on the fibrinogen solution that has undergone the viral inactivation treatment, so the viral inactivation solution is in the non-adsorbed chromatography fraction and is removed at the same time as the fibrinogen is purified.

In the process in accordance with the invention, the elution buffer comprises arginine; the arginine concentration is preferentially at least 200 mM, at least 300 mM, at least 400 mM, at least 500 mM, at least 600 mM, at least 700 mM, at least 800 mM, at least 900 mM, at least 1 M.

In a preferred embodiment, the arginine concentration of the elution buffer is preferentially comprised between 200 and 800 mM, between 200 and 700 mM, between 200 and 600 mM, between 200 and 500 mM, between 200 and 400 mM, between 200 and 300 mM.

In another embodiment, the arginine concentration of the elution buffer is preferentially comprised between 300 and 800 mM, between 400 and 800 mM, between 500 and 800 mM, between 600 and 800 mM, between 700 and 800 mM.

In another embodiment, the arginine concentration of the elution buffer is preferentially comprised between 300 and 800 mM, between 400 and 700 mM, between 400 and 600 mM.

In the process in accordance with the invention, the elution buffer may also contain other suitable excipients, such as salts and/or amino acids, for example trisodium citrate, Tris, lysine, glycine, and/or isoleucine.

In another particular embodiment of the invention, the elution buffer may consist of either a change in pH and/or ionic strength.

In another particular embodiment of the invention, the composition comprising fibrinogen is derived from milk of transgenic animals, for example obtained according to the method described in WO00/17234 or in WO00/17239.

Advantageously, the fibrinogen composition subjected to the process in accordance with the invention has a purity greater than or equal to 70%, preferably greater than or equal to 75%, 80%, 85%, 90%, 95%, 96%, 97%, 98%, 99%.

In a particular embodiment of the invention, the fibrinogen composition subjected to the process in accordance with the invention advantageously does not comprise other co-purified proteins, advantageously no FXIII and/or fibronectin and/or prothrombin (FII) and/or thrombin, and/or plasminogen and/or plasmin. In a particular embodiment of the invention, the fibrinogen composition subjected to the process in accordance with the invention is advantageously free of FXIII.

In accordance with the invention, the fibrinogen composition subjected to the process in accordance with the invention may also comprise one or more accompanying, optionally co-purified, proteins. In a particular embodiment of the invention, the fibrinogen composition subjected to the process in accordance with the invention advantageously comprises FXIII.

In a particularly advantageous embodiment of the invention the fibrinogen composition subjected to the process in accordance with the invention does not comprise multimeric forms of fibrinogen, advantageously no fibrinogen polymers or fibrinogen aggregates.

Particularly advantageously, the fibrinogen composition subjected to the process in accordance with the invention is concentrated to more than 1 g fibrinogen/L solution, preferably to more than 2 g fibrinogen/L solution, even more preferably to more than 3 g fibrinogen/L solution, to more than 3.5 g fibrinogen/L solution, to more than 4 g fibrinogen/L solution, to more than 4.5 g fibrinogen/L solution. In a particular embodiment of the invention, the fibrinogen composition subjected to the process in accordance with the invention is concentrated between 2 g and 5 g fibrinogen/L solution. Furthermore, preferably, it is used without prior dilution. Indeed, preferably, the process in accordance with the invention does not require a step of prior dilution of the fibrinogen composition.

The process in accordance with the invention optionally comprises a step b), according to which at least one step of filtering the fibrinogen is carried out on a filter having a pore size comprised between 0.08 μm and 0.22 μm.

Preferably, step b) comprises two steps of filtering the fibrinogen on a filter having a pore size comprised between 0.08 μm and 0.22 μm. Preferably, the first filtration is performed on a filter having a pore size comprised between 0.15 μm and 0.22 μm, preferably about 0.2 μm. Preferably, the second filtration is performed on a filter having a pore size comprised between 0.08 μm and 0.15 μm, preferably about 0.1 μm.

These filtrations can be performed using polyethersulfone (PES) filters marketed by the company SARTORIUS under the name Sartopore® 2 MaxiCaps® or any other equivalent media with similar features.

Preferably, the filter sequence is, prior to step b), equilibrated with the buffer from the previous purification steps, in particular with the elution buffer from the chromatography, optionally supplemented with amino acids.

At the end of step b), a fibrinogen composition is recovered.

Then, the process in accordance with the invention comprises filtering the fibrinogen composition optionally obtained in b), on a symmetrical filter having a pore size comprised between 15 nm and 25 nm: this is step c).

If step b) is performed, then the fibrinogen solution obtained in b) is passed over a symmetrical filter having pores of diameter comprised between 15 nm and 25 nm, preferentially 20 nm, and the resulting fibrinogen solution is recovered. If step b) is not performed, then the fibrinogen composition obtained by elution chromatography in step a) is directly passed over a symmetric filter having pores of diameter comprised between 15 nm and 25 nm, preferentially 20 nm, and the resulting fibrinogen solution is recovered.

The nanofiltration of step c) is typically performed at a pressure comprised between 200 and 4000 mbar. Advantageously, the nanofiltration of step b) is typically performed at a pressure comprised between 200 and 1000 mbar, or between 2000 and 4000 mbar.

Advantageously, the filters used can be defined by their average pore size in nm, by the viruses retained by the filter, by a molecular weight threshold or by the type of symmetry of their membrane. The filters used can therefore be filters, or any other equivalent filter on the market:

defined by an average pore size in nm, including filters from the PLANOVA™ range, consisting of a hollow-fiber membrane formed of cuprammonium-regenerated cellulose and marketed by the company ASAHI KASEI BIOPROCESS (PLANOVA™ 15N, PLANOVA™20N), and those from the ULTIPOR®® range, composed of a surface-modified polyvinylidene fluoride membrane and marketed by the company Pall® (ULTIPOR® DV20, Pegasus SV4), or any other commercially-available equivalent filter;

whose average pore size is defined relative to the viruses retained by the filter. The average pore size of the filter then corresponds to the size of the smallest virus retained by the filter. Such filters, defined by the viruses retained by the filter, include PLANOVA™ BIOEX® PVDF filters (parvovirus retention, hydrophilic modified polyvinylidene fluoride membrane) marketed by the company ASAHI KASEI BIOPROCESS, Pegasus SV4 or ULTIPOR® VF filters (parvovirus retention, hydrophilic modified polyvinylidene fluoride membrane) marketed by the company Pall®, VIRESOLVE® NFP filters (parvovirus retention, surface-modified polyvinylidene fluoride membrane), VIRESOLVE® Pro filters (parvovirus retention, double-layer polyethersulfone membrane) and VIRESOLVE® NFR filters (retrovirus retention, polyethersulfone membrane) marketed by the company MILLIPORE®, and VIROSART® CPV (canine parvovirus retention, double-layer polyethersulfone membrane), VIROSART® HC or VIROSART® HF filters marketed by the company SARTORIUS, or any other commercially-available equivalent filter. These filters, which are defined by the viruses retained, in particular parvoviruses, have an average pore size of about 20 nm.

defined by their symmetry, for example asymmetrical filters such as the filters of the PLANOVA™ range, marketed by the company ASAHI KASEI BIOPROCESS (PLANOVA™ 15N, PLANOVA™ 20N, PLANOVA™ BIOEX®), VIRESOLVE® NFP and VIRESOLVE(®) Pro (marketed by the company MERK MILLIPORE®), VIROSART® HF (marketed by the company SARTORIUS Stedim).

symmetrical filters, such as the Pegasus SV4 or ULTIPOR® DV20 filter (marketed by the company Pall®), the VIROSART® CPV filter (marketed by the company SARTORIUS Stedim).

Such a classification of filters according to their symmetry appears in particular in Gustafsson et al., "Mille-feuille paper: a novel type of filter architecture for advanced virus separation applications." Materials Horizons 2016, 3, 320-337.

"Symmetrical filter", in accordance with the invention, means a filter with an equivalent porosity between the inner surface (in contact with the solution to be filtered) and the outer surface of the filter. This is in contrast to asymmetrical filters where the inner surface of the filter is often more porous than the outer surface.

Regardless of how the filter is defined by the manufacturer, the pore size in nm can be measured by the skilled person using known techniques.

In a particularly advantageous embodiment, the nanofiltration carried out in step c) is performed using a symmetric type filter.

Preferably, the nanofiltration in step c) is performed using a symmetric filter, such as the Pegasus SV4 or ULTIPOR® DV20 filter (marketed by the company Pall®), the VIROSART® CPV filter (marketed by the company SARTORIUS Stedim).

In a particular embodiment, the symmetric filter is in a pleated arrangement.

In another particular embodiment, the symmetrical filter is advantageously characterized by a hydrophilic polyvinylidene fluoride (PVDF) membrane.

In a particular embodiment, the symmetrical filter in a pleated arrangement characterized by a hydrophilic polyvinylidene fluoride (PVDF) membrane is a Pegasus SV4 filter (marketed by the company Pall®).

The applicant has advantageously demonstrated that filters of symmetrical type, such as filters similar to the Pegasus SV4 or ULTIPOR® DV20 filter (marketed by the company Pall®) or VIROSART® CPV filter (marketed by the company SARTORIUS Stedim) make it possible to carry out fibrinogen nanofiltration with a load of at least 0.2 kg fibrinogen/$m^2$ membrane, said fibrinogen composition not being previously frozen and/or thawed, and to obtain better results than with an asymmetrical type filter such as the filters of the PLANOVA™ range, marketed by the company ASAHI KASEI BIOPROCESS(PLANOVA™ 15N, PLANOVA™ 20N).

As shown in the examples, this step c) allows a substantial volume of fibrinogen solution to be filtered, with a particularly good yield, i.e., at least equal to 90%. This substantial volume corresponds to a capacity of at least 0.2 kg fibrinogen per $m^2$ and can go up to at least 5 kg per $m^2$.

As shown in example 7, the filtration capacity of a fibrinogen composition is advantageously increased by adding increasing concentrations of arginine to the elution buffer of the chromatography performed prior to the filtration sequence.

In a preferred embodiment of the filtration process in accordance with the invention, the elution buffer of the chromatography performed in step a) comprises an arginine concentration of at least 200 mM and said filtration process has a capacity of at least 0.25 kg/$m^2$.

In another embodiment of the filtration process in accordance with the invention, the elution buffer of the chromatography performed in step a) comprises an arginine concentration of at least 200 mM and said filtration process has a capacity of at least 0.30 kg/$m^2$.

In another embodiment, the elution buffer of the chromatography performed in step a) comprises an arginine concentration of at least 200 mM and said filtration process has a capacity of at least 0.35 kg/$m^2$.

In another embodiment of the invention, the elution buffer of the chromatography performed in step a) comprises an arginine concentration of at least 400 mM and said filtration process has a capacity of at least 0.25 kg/$m^2$.

In another embodiment of the invention, the elution buffer of the chromatography performed in step a) comprises an arginine concentration of at least 400 mM and said filtration process has a capacity of at least 0.30 kg/$m^2$. In another embodiment, the elution buffer of the chromatography performed in step a) comprises an arginine concentration of at least 400 mM and said filtration process has a capacity of at least 0.35 kg/$m^2$.

The filtration capacity is measured by any method known to the person skilled in the art. Typically, it is determined as follows:

The fibrinogen solution to be nanofiltered is prepurified by chromatography according to the method described in EP1739093. The concentration of the starting fibrinogen solution is 3 g/L.

With a view to determining the filtration capacity, increasing amounts of fibrinogen are applied to the nanofiltration sequence.

A filtration sequence for this eluate is applied:

0.2-0.1 μm polyethersulfone filter 35 nm filter (PLANOVA™ 35 N type, from the company ASAHI-KASEI BIOPROCESS)

20 nm symmetrical filter (Pegasus SV4 type from the company Pall® Life Sciences) The filtration is performed at a constant pressure of 2.1 bar on the 20 nm filter. The filtration capacity of the filter is determined by analysis of the clogging profile; the maximum filtration capacity corresponds to the amount of fibrinogen associated with a filtration rate less than 25% of the initial flow rate.

Mention may also be made of the method described by Burnouf et al. (Haemophilia. 2003 January;9(1):24-37).

Preferably, the process for filtering a fibrinogen composition in accordance with the invention comprises the following steps:

A) obtaining the fibrinogen composition, said fibrinogen composition being selected from a cell culture supernatant, milk from transgenic animals, cryoprecipitated plasma supernatant, resuspended plasma cryoprecipitate, fraction I obtained by ethanol fractionation according to the Cohn or the Kistler & Nitschmann method, the supernatant and precipitate obtained after precipitation of a plasma fraction with aluminum hydroxide and/or low-temperature precipitation, and the eluates of chromatography and the non-adsorbed fractions of chromatography columns obtained from a plasma fraction, a cell culture supernatant or milk of transgenic animals, a) passing the composition obtained in A) through an affinity, mixed-mode or ion-exchange chromatography and eluting in buffer comprising arginine

11 b) at least one step of filtering the fibrinogen composition obtained in a), on a filter having a pore size comprised between 0.08 µm and 0.22 µm, c) filtering the fibrinogen solution obtained in b), on a symmetrical filter having a pore size comprised between 15 nm and 25 nm, and d) recovering the resulting fibrinogen solution, said filtration process being carried out, without addition of arginine after step a), at high capacity and said fibrinogen composition not being previously frozen and/or thawed.

Preferably, the process for filtering a fibrinogen composition in accordance with the invention comprises the following steps:

A) obtaining a cryoprecipitated plasma supernatant or a resuspended plasma cryoprecipitate, a) passing the composition obtained in A) over an affinity chromatography, preferably an aptamer ligand affinity chromatography, and eluting in buffer comprising arginine b) at least one step of filtering the fibrinogen composition obtained in a), on a filter having a pore size comprised between 0.08 µm and 0.22 µm, c) filtering the fibrinogen solution obtained in b), on a symmetrical filter having a pore size comprised between 15 nm and 25 nm, and d) recovering the resulting fibrinogen solution, said filtration process being carried out without addition of arginine after step a), at high capacity and said fibrinogen composition not being previously frozen and/or thawed.

In a particular embodiment of the invention, the fibrinogen solution optionally obtained in b) is passed over a filter having pores of diameter comprised between 15 nm and 50 nm prior to step c): this is step b').

Advantageously, the filters used can be defined by their average pore size in nm, by the viruses retained by the filter, by a molecular weight threshold or by the type of symmetry of their membrane. The filters used can therefore be filters, or any other commercially-available equivalent filter:

defined by an average pore size in nm, including filters from the PLANOVA™ range, consisting of a hollow-fiber membrane formed of cuprammonium-regenerated cellulose and marketed by The company ASAHI KASEI BIOPROCESS(PLANOVA™ 15N, PLANOVA™ 20N), and those from the ULTIPOR@® range, composed of a surface-modified polyvinylidene fluoride membrane and marketed by the company Pall® (ULTIPOR® DV20, Pegasus SV4), or any other commercially-available equivalent filter;

whose average pore size is defined relative to the viruses retained by the filter. The average pore size of the filter then corresponds to the size of the smallest virus retained by the filter. Such filters, defined by the viruses retained by the filter, include PLANOVA™ BIOEX® PVDF filters (parvovirus retention, hydrophilic modified polyvinylidene fluoride membrane) marketed by the company ASAHI KASEI BIOPROCESS, Pegasus SV4 or ULTIPOR® VF filters (parvovirus retention, hydrophilic modified polyvinylidene fluoride membrane) marketed by the company Pall®, VIRESOLVE® NFP filters (parvovirus retention, surface-modified polyvinylidene fluoride membrane), VIRESOLVE® Pro filters (parvovirus retention, double-layer polyethersulfone membrane) and VIRESOLVE® NFR filters (retrovirus retention, polyethersulfone membrane) marketed by MILLIPORE®, and VIROSART® CPV (canine parvovirus retention, double-layer polyethersulfone membrane), VIROSART® HC or VIROSART® HF filters marketed by The company SARTORIUS, or any other commercially-available equivalent filter. These filters, which are defined by the viruses retained, in particular parvoviruses, have an average pore size of about 20 nm.

defined by their symmetry, for example asymmetrical filters such as the filters of the PLANOVA™ range, marketed by the company ASAHI KASEI BIOPROCESS(PLANOVA™ 15N, PLANOVA™ 20N, PLANOVA™ BIOEX®), VIRESOLVE® NFP and VIRESOLVE® Pro filters (marketed by the company MERK MILLIPORE®), VIROSART® HF filters (marketed by The company SARTORIUS Stedim).

symmetrical filters, such as the Pegasus SV4 or ULTIPOR® DV20 filter (marketed by the company Pall®), the VIROSART® CPV filter (marketed by The company SARTORIUS Stedim).

Such a classification of filters according to their symmetry appears in particular in Gustafsson et al., "Mille-feuille paper: a novel type of filter architecture for advanced virus separation applications." Materials Horizons 2016, 3, 320-337.

"Symmetrical filter", in accordance with the invention, means a filter with equivalent porosity between the inner surface (in contact with the solution to be filtered) and the outer surface of the filter.

According to a particular embodiment of the process, the nanofiltration of step b') is carried out using filters with a pore diameter comprised between 25 nm and 50 nm, preferentially 35 nm. Preferably, the nanofiltration of step b') is then performed using the PLANOVA™ 35 N filter marketed by the company ASAHI KASEI BIOPROCESS or STyLUX® marketed by the company MEISSNER (40 nm).

Alternatively, the nanofiltration of step b') is performed using symmetric filters with a pore diameter comprised between 15 nm and 25 nm, preferentially 20 nm. Preferably, the nanofiltration of step b') is then performed using a symmetric membrane filter, such as the Pegasus SV4 or ULTIPOR® DV20 filter (marketed by the company Pall®) or VIROSART® CPV filter (marketed by the company SARTORIUS Stedim).

In a particular embodiment of the invention, the nanofiltration of step b') and of step c) is performed on filters of decreasing porosity, advantageously on a 35 nm porosity filter followed by a symmetrical 20 nm porosity filter. Preferably, the nanofiltration of step b') is then carried out using the PLANOVA™ 35 N filter marketed by the company ASAHI KASEI BIOPROCESS followed by a symmetrical membrane filter, such as the Pegasus SV4 or ULTIPOR® DV20 filter (marketed by the company Pall®) or VIROSART® CPV filter (marketed by the company SARTORIUS Stedim).

In another particular embodiment of the invention, the nanofiltration of step b') and of step c) is performed on filters of the same pore size, advantageously on two identical filters. Preferably, the nanofiltration of step b') is then performed using a symmetrical membrane filter, such as the Pegasus SV4 or ULTIPOR® DV20 filter (marketed by The company Pall®) or VIROSART® CPV filter (marketed by The company SARTORIUS Stedim).

The nanofiltration of step b') is typically performed at a pressure comprised between 200 and 4000 mbar. Advantageously, the nanofiltration of step b') is typically performed at a pressure comprised between 200 and 1000 mbar, or between 2000 and 4000 mbar.

Thus, preferably, the invention relates to a process for filtering a fibrinogen composition, comprising the following steps:

a) chromatographic purification of the fibrinogen composition using an elution buffer comprising arginine:

b) at least one step of filtering the fibrinogen composition, on a filter having a pore size comprised between 0.08 μm and 0.22 μm, and recovering the resulting fibrinogen solution, b') filtering the fibrinogen solution obtained in b), on a filter with a pore diameter comprised between 15 nm and 50 nm, c) filtering the fibrinogen solution obtained in b'), on a symmetrical filter with a pore size comprised between 15 nm and 25 nm, and d) recovering the resulting fibrinogen solution, said filtration process being carried out without addition of arginine after step a), at high capacity and said fibrinogen composition not being previously frozen and/or thawed.

At the end of step d), the solution obtained comprises fibrinogen, and is highly safe.

Particularly advantageously, the implementation of step c) of the process in accordance with the invention allows the removal of at least 2 log, advantageously at least 3 log, even more advantageously at least 4 log, preferentially at least 5 log or at least 6 log of small-sized viruses such as parvovirus B119.

Preferably, the process for filtering a fibrinogen composition in accordance with the invention comprises the following steps:

A) obtaining the fibrinogen composition, said fibrinogen composition being selected from a cell culture supernatant, milk from transgenic animals, cryoprecipitated plasma supernatant, resuspended plasma cryoprecipitate, fraction I obtained by ethanol fractionation according to the Cohn or the Kistler & Nitschmann method, the supernatant and precipitate obtained after precipitation of a plasma fraction with aluminum hydroxide and/or low-temperature precipitation, and the eluates of chromatography and the non-adsorbed fractions of chromatography columns obtained from a plasma fraction, a cell culture supernatant or milk from transgenic animals, a) passing the composition obtained in A) through an affinity, mixed-mode or ion-exchange chromatography and eluting in buffer comprising arginine, b) at least one step of filtering the fibrinogen composition obtained in A), on a filter having a pore size comprised between 0.08 μm and 0.22 μm, b') filtering the fibrinogen solution obtained in b), on a filter having a pore diameter comprised between 15 nm and 50 nm, c) filtering the fibrinogen solution obtained in b'), on a symmetrical filter having a pore size comprised between 15 nm and 25 nm, and d) recovering the resulting fibrinogen solution, said filtration process being carried out without addition of arginine after step a), at high capacity and said fibrinogen composition not being previously frozen and/or thawed.

Preferably, the process for filtering a fibrinogen composition in accordance with the invention comprises the following steps:

A) obtaining a cryoprecipitated plasma supernatant or a resuspended plasma cryoprecipitate, a) passing the composition obtained in A) over an affinity chromatography, preferably an aptamer ligand affinity chromatography, and eluting in buffer comprising arginine, b) at least one step of filtering the fibrinogen composition obtained in a), on a filter having a pore size comprised between 0.08 μm and 0.22 μm, c) filtering the fibrinogen solution obtained in b), on a symmetrical filter having a pore size comprised between 15 nm and 25 nm, and d) recovering the resulting fibrinogen solution, said filtration process being carried out without addition of arginine after step a), at high capacity and said fibrinogen composition not being previously frozen and/or thawed.

The solution obtained in step d) can then be concentrated, for example by ultrafiltration, to contents typically comprised between 10 and 40, preferentially between 15 and 25 g of total protein/L, determined by conventional measurements known to the skilled person.

In addition, the fibrinogen solution obtained, optionally concentrated, can be subjected to a diafiltration step. This step is intended to remove the possible excess of inorganic salt used to obtain solutions having an ionic strength of at most 0.2 M. This step may also be necessary in order to formulate the fibrinogen under optimal conditions. The buffer is advantageously suitable either for preservation of the fibrinogen composition in liquid form (ready-to-use liquid formulation) or for preservation in freeze-dried form (formulation suitable for preservation during the freeze-drying step and optionally the dry heating step). This allows, in this case, on the one hand, a dry heating of the fibrinogen without risk of denaturation and, on the other hand, a fast solubilization when the fibrinogen is subsequently freeze-dried, typically in 3 to 8 minutes.

The respective solutions, optionally diafiltered, optionally concentrated, can be optionally freeze-dried according to conventional methods and usual conditions. The lyophilizates can then be reconstituted in an aqueous medium compatible with clinical use, preferably in purified water for injection (WFI), and directly injected intravenously.

At least one additional step of removing or inactivating at least one infectious agent and contaminants, such as viruses, bacteria, or non-conventional transmissible agents such as prions, may be provided.

Viral inactivation often includes treatment with chemicals, for example by solvent and/or detergent and/or heat (pasteurization and/or dry heating) and/or irradiation (gamma rays and/or UVC). This step can be carried out by a conventional chemical viral inactivation treatment, preferably consisting of a solvent-detergent (generally called S/D) treatment. The chemical viral inactivation agents are preferably mixtures of polysorbate and Tri(n-butyl)phosphate (TnBP), or mixtures of Triton (octoxinol) and TnBP, whose typical concentrations are comprised between 0.1% and 2%. This viral inactivation can be incorporated in any step of the process, but it is judiciously implemented before the chromatographic purification step a). In this way, it will contribute to the efficient removal of the inactivation agents.

Alternatively, an additional dry-heat viral inactivation treatment step can be used, performed on the fibrinogen lyophilizates obtained after the freeze-drying step. The operating conditions are conventionally about 80° C. for 72 hours.

The removal of infectious agents can also be achieved by means of depth filtration. Available filters are, for example, filters made of regenerated cellulose, to which filter aids such as celite, perlite or kieselguhr may have been added. Such filters are in particular marketed by Cuno (Zeta+ VR series filters), the company Pall®-Seitz (P-series Depth Filter) or the company SARTORIUS (SARTOCLEAR® P depth filters).

Thus, the implementation of the process leads to highly safe fibrinogen solutions, free of viral particles and/or non-conventional transmissible agent-type contaminants.

The invention therefore has as its object a fibrinogen solution obtainable by the process described above.

The fibrinogen solution obtainable by the process described above advantageously has a purity greater than or equal to 95% and is advantageously stable without the addition of a stabilizing protein such as albumin.

The fibrinogen solution obtainable by the process described above advantageously has an integral fibrinogen activity with, in particular, a coagulable fibrinogen/antigenic fibrinogen ratio of >0.9, or even equal to 1.0.

The following examples illustrate an embodiment of the present invention without however limiting the scope thereof.

EXAMPLES

Example 1: Evaluation of Fibrinogen Filtration on a 20 nm Symmetrical Filter in Accordance with the Invention The composition comprising prepurified fibrinogen is obtained according to the method described in EP1739093.

I—Objectives

To evaluate the filterability of a composition comprising fibrinogen on a symmetrical nanofiltration filter with a pore size of about 20 nm.

II—Operating Parameters

Filtration sequence
    0.2-0.1 μm polyethersulfone (PES) filter
    20 nm symmetrical Pegasus SV4 filter from The company Pall® Life Sciences, surface area 0.00096 m$^2$ (Pegasus VF SV4, 10MCFSV4, surface area 9.6 cm$^2$).
    The solution containing fibrinogen is concentrated to 3 g/L and is more than 90% pure.

TABLE 1

| Steps/Parameters | 20 nm filter evaluation |
|---|---|
| Raw material | Fibrinogen chromatography eluate obtained according to EP1739093 eluted in buffer comprising 200 mM arginine |
| Filtration sequence | 0.2-0.1 μm PES 20 nm 0.00096 m$^2$ |
| Total protein g/L | 2.7 |
| Pressure mbar | 2110 ± 10 (on 20 nm filter) |

III—Results

The filtration pressure was kept constant at 2.1 bar on the 20 nm filter throughout the filtration.

The filtration sequence is equilibrated in ion-exchange elution chromatography buffer described in patent EP1739093 comprising arginine. The fibrinogen clogging profile on the 20 nm pore size filter is linear with a decrease proportional to the filtered volume up to 181 L/m$^2$.

After 10 hours 15 minutes of filtration corresponding to an optimal use of the filter, a weight of 178 g of solution was collected; at this stage, the ratio of filtration rate/initial flow rate is 19%. The calculated average filtration rate of 0.3 g/min corresponds to about 17 L/h/m$^2$ of membrane.

IV—Summary Table of Results

TABLE 2

| Steps/Parameters | Results |
|---|---|
| Filtration time | 10 h 15 |
| Capacity of the sequence kg/m$^2$ | 185 |
| Ratio final/initial flow rate % | 19 |
| Average flow rate kg/h/m$^2$ | 18 |
| Antigenic fibrinogen g/L | ND |
| Capacity of the sequence kg protein/m$^2$ | 0.5 |

The applied filtration sequence allowed the filtration of an amount equivalent to 0.5 kg fibrinogen per m$^2$ of 20 nm pore size membrane in 6 hours. Higher filterabilities could have been achieved by extending the filtration time.

By virtue of the process in accordance with the invention, the yield of this nanofiltration is higher than 90%.

The process in accordance with the invention thus allows the filterability, on a symmetrical filter with a pore size of about 20 nm, of a composition comprising fibrinogen without a prior freezing/thawing step, nor prior dilution from a solution of fibrinogen prepurified by chromatography, eluted by a buffer comprising arginine.

Example 2: Evaluation of Fibrinogen Filtration on Symmetrical 20 nm Pall® DV 20 Filter in Accordance with the Invention The composition comprising prepurified fibrinogen is obtained according to the method described in the application EP1739093.

I—Objectives

To evaluate the filterability of a composition comprising fibrinogen on a symmetrical nanofiltration filter with a pore size of about 20 nm.

II—Operating Parameters

Filtration Sequence
    0.2-0.1 μm polyethersulfone (PES) filter
    20 nm symmetrical ULTIPOR® VF DV20 filter from The company Pall® Life Sciences, surface area 0.00106 m$^2$.
    The solution containing fibrinogen is concentrated to 3.1 g/L and more than 90% pure.

TABLE 3

| Steps/Parameters | 20 nm filter evaluation |
|---|---|
| Raw material | Fibrinogen chromatography eluate obtained according to EP1739093 eluted in buffer comprising 200 mM arginine |

TABLE 3-continued

| Steps/Parameters | 20 nm filter evaluation |
|---|---|
| Filtration sequence | 0.2-0.1 µm PES |
| | 20 nm 0.00106 m² |
| Total protein g/L | 3.1 |
| Pressure mbar | 2027 ± 7 (on 0.2-0.1 µm filter) |
| | 2025 ± 39 (on 20 nm filter) |

III—Results

The filtration pressure was kept constant at 2.0 bar on the 20 nm filter throughout the filtration.

The filtration sequence is equilibrated in ion-exchange elution chromatography buffer described in the patent EP1739093 comprising arginine. The fibrinogen clogging profile on the 20 nm pore size filter is linear with a decrease proportional to the filtered volume up to 136 L/m².

After 16 hours 30 minutes of filtration corresponding to an optimal use of the filter, a weight of 154.7 g of solution was collected; at this stage, the ratio of filtration rate/initial flow rate is 27%. The calculated average filtration rate of 0.1 g/min corresponds to about 9 L/h/m² of membrane.

IV—Summary Table of Results

TABLE 4

| Steps/Parameters | Results |
|---|---|
| Filtration time h | 16 h 30 |
| Capacity of the sequence kg/m² | 146 |
| Ratio final/initial flow rate % | 27 |
| Average flow rate kg/h/m² | 8.8 |
| Antigenic fibrinogen g/L | 3.1 |
| Capacity of the sequence kg fibrinogen/m² | 0.4 |

The applied filtration sequence allowed the filtration of an amount equivalent to 0.4 kg of fibrinogen per m² of 20 nm pore size membrane in 15 hours. Higher filterabilities could have been achieved by extending the filtration time.

Example 3: Evaluation of Fibrinogen Filtration on 20 nm Symmetrical Filter in Accordance with the Invention with 20-50 nm Prefiltration The composition comprising prepurified fibrinogen is obtained according to the method described in the application EP1739093.

I—Objectives

To evaluate the filterability of a composition comprising fibrinogen on a symmetrical nanofiltration filter with a pore size of about 20 nm.

II—Operating Parameters

Filtration Sequence
0.2-0.1 µm polyethersulfone (PES) filter
35 nm filter (PLANOVA™35N from the company ASAHI KASEI BIOPROCESS)
20 nm symmetrical Pegasus SV4 filter from The company Pall® Life Sciences, surface area 0.00096 m² (Pegasus VF SV4, 10MCFSV4, surface area 9.6 cm²).
The solution containing fibrinogen is concentrated to 3 g/L and is more than 90% pure.

TABLE 5

| Steps/Parameters | 20 nm filter evaluation |
|---|---|
| Raw material | Fibrinogen |
| | chromatography eluate obtained according to EP1739093 |
| | eluted in buffer comprising 200 mM arginine |
| Filtration sequence | 0.2-0.1 µm PES |
| | 35 nm 0.01 m2 + 20 nm 0.00096 m² |
| Total protein g/L | 3.1 |
| Pressure mbar | 300 ± 50 (on 35 nm filter) |
| | 2100 ± 100 (on 20 nm filter) |

III—Results

The filtration pressure was kept constant at 2.1 bar on the 20 nm filter throughout the filtration.

The filtration sequence is equilibrated in ion-exchange elution chromatography buffer described in the patent EP1739093. The fibrinogen clogging profile on the 20 nm pore size filter is linear with a decrease proportional to the filtered volume up to 276 L/m².

After 18 hours of filtration corresponding to an optimal use of the filter, a weight of 264.8 g of solution was collected; at this stage, the ratio of filtration rate to initial flow rate is 14%. The calculated average filtration rate of 0.3 g/min corresponds to about 15 L/h/m² of membrane.

IV—Summary Table of Results

TABLE 6

| Steps/Parameters | Results |
|---|---|
| Filtration time h | 18 |
| Capacity of the sequence kg/m² | 290 |
| Ratio final/initial flow rate % | 14 |
| Average flow rate kg/h/m² | 16.1 |
| Antigenic fibrinogen g/L | 3.0 |
| Capacity of the sequence kg fibrinogen/m² | 0.8 |

The applied filtration sequence allowed the filtration of an amount equivalent to 0.8 kg of fibrinogen per m² of 20 nm pore size membrane in 18 hours.

By virtue of the process in accordance with the invention, the yield of this nanofiltration is higher than 90%.

The process in accordance with the invention thus allows the filterability, on a symmetrical filter with a pore size of about 20 nm, of a composition comprising fibrinogen without a prior freezing/thawing step, or prior dilution from a solution of fibrinogen prepurified by chromatography, eluted by a buffer comprising arginine.

Example 4: Comparison of the Process in Accordance with the Invention with a Prior Art Process on Asymmetrical Filter of about 20 nm

I—Objectives

To compare the level of fibrinogen capacity per m² of membrane that can be supported by the process in accordance with the invention and a prior art process on asymmetrical filter of about 20 nm.

II—Preparation of the Raw Material

The composition comprising prepurified fibrinogen is obtained according to the method described in the application EP1739093. The chromatography eluate obtained according to EP1739093 is eluted in buffer comprising 200 mM arginine.

III—Preparation of the Filter Equilibration Buffer

This is the same elution buffer as that used for the preparation of the starting eluate (Tp E DEAE Macro-Prep, adjusted to pH 7.5±0.1 with 1 M citric acid).

IV—Filtration Sequence

1. Prefiltration:

The fibrinogen composition is prefiltered using a polyether sulfone (PES) filter model Sartopore 2 with a porosity of 0.2-0.1 µm (100 nm).

2. Filtration:

Depending on the operating condition tested the prefiltered composition is then filtered:

using a Pegasus SV4 filter (marketed by The company Pall® Life Sciences) at 2100±100 mbar, or using a PLANOVA™ 20N filter (marketed by the company ASAHI KASEI BIOPROCESS) at 395±23 mbar.

invention" in the following graph), in this case using a symmetric Pegasus SV4 filter from The company Pall® Life Sciences.

Thus, these results illustrate that the application of the prior art process on an asymmetrical filter does not allow a filtration capacity of 200 $g/m^2$ membrane to be obtained, with in particular a fibrinogen capacity of 55 $g/m^2$ obtained on PLANOVA™ 20N membrane from the company ASAHI KASEI BIOPROCESS.

Example 5: Comparison of the Process in Accordance with the Invention on Symmetrical Filter with the Prior Art Processes on Asymmetrical Filter Under the same conditions as example 4, different asymmetrical filters of the prior art processes are tested in comparison with the process in accordance with the invention.

The results are as follows:

TABLE 7

| | Process according to the invention on symmetrical filters | | | Process according to the prior art on asymmetrical filters | | | |
|---|---|---|---|---|---|---|---|
| | Pegasus S4 | ULTIPOR® VF company | PLANOVA™ 35N ASAHI KASEI BIO-PROCESS + The | | | | |
| | The company Pall® (example 1) | Pall® DV20 The (example 2) | company Pall@ SV4 (example 3) | PLANOVA™ 20N IOPROCESS (example 4) | PLANOVA™ BIOEX® IOPROCESS | VIRESOLVE® NFP MILLIPORE® | VIROSART® HF the company SARTORIUS |
| Filtration time h | 10 h 15 | 16 h 30 | 18 | 2.5 | 3.7 | 2.0 | 1.33 |
| Capacity of the sequence kg solution/m² | 185 | 146 | 290 | 17 | 00 | 6.6 | 10.2 |
| Ratio final/initial flow rate % | 19 | 27 | 14 | 19 | 6 | 7 | 8 |
| Average flow rate kg/h/m² | 18 | 8.8 | 16.1 | 6.8 | 4.9 | 3.3 | 7.7 |
| Antigenic fibrinogen g/L | 2.7 | 3.1 | 3.0 | 3.4 | 3.4 | 3.2 | 3.2 |
| Sequence capacity kg fibrinogen/m² | 0.5 | 0.4 | 0.8 | 0.055 | 0.061 | 0.020 | 0.031 |

V—Results

The results obtained have been compiled in the graph as shown in FIG. 1.

For both processes, it is observed that the lower the flow rate (in $L/h/m^2$) applied, the more the supported fibrinogen capacity (in g of fibrinogen per $m^2$ of membrane) increases.

However, it can be observed that the fibrinogen capacity supported by the prior art process ("prior process" in the following graph), in this case using an asymmetrical PLANOVA™20N filter from the company ASAHI KASEI BIOPROCESS, is much lower than that supported by the process in accordance with the invention ("process of the Asymmetrical nanofilters tested on a chromatographically prepurified fibrinogen solution with a concentration of at least 2 g/L show filterabilities of less than 0.1 kg fibrinogen per $m^2$, whereas the process in accordance with the invention on a symmetrical filter makes it possible to achieve a filterability greater than 0.2 kg fibrinogen per $m^2$.

Example 6: Evaluation of Viral Reduction

I—Objective

To evaluate the viral reduction obtained using the process in accordance with the invention.

II—Preparation of the Raw Material

The composition comprising prepurified fibrinogen is obtained according to the method described in the application EP1739093.

III—Preparation of the Filter Equilibration Buffer

This is the same elution buffer as that used for the preparation of the starting eluate (Tp E DEAE Macro-Prep, adjusted to pH 7.5±0.1 with 1 M citric acid).

IV—Filtration Sequence

The fibrinogen composition is prefiltered using a Minisart High Flow model polyether sulfone (PES) filter with a porosity of 0.2-0.1 μm (100 nm).

Nanofiltration is performed on the The company Pall® Life Sciences Pegasus SV4 filter at a pressure of 2.1±0.1 bar.

Viral load is measured is produced using PPV Ultrapure Gold 1% (v/v).

A sample is taken from the nanofiltered fraction after filtration of 79.2 $L/m^2$ of solution (loaded volume).

A complete clogging of the filter is observed after filtration of 85.5 L loaded per $m^2$ of membrane.

V—Results

The results obtained are presented in the table below.

These results show that for a fibrinogen capacity of 250 $g/m^2$ of membrane, the measured viral reduction is 3.78 (±0.56) log 10.

| VI - Summary table of results | | | | |
|---|---|---|---|---|
| Volume loaded ($L/m^2$) | Cumulative fibrinogen load ($g/m^2$) | Input viral load (log 10 TCID50) | Output viral load (log 10 TCID50) | Viral reduction factor (log 10) |
| 79.2 | 253 | 8.11 ± 0.17 | 4.33 ± 0.22 | 3.78 ± 0.56 |

Example 7: Evaluation of the Filtration Capacity of Fibrinogen on a Nm Symmetrical Filter as a Function of Increasing Arginine Concentrations in the Elution Buffer of the Chromatography Step

I—Objectives

To evaluate the filtration capacity of fibrinogen with increasing concentrations of arginine added in the elution buffer of the chromatography step prior to the filtration sequence.

II—Operating Parameters

The fibrinogen compositions tested are prepurified by affinity chromatography according to the method described in the application EP1739093, using an elution buffer comprising 50 mM sodium citrate and increasing concentrations of arginine HCL (150 mM, 200 mM, 400 mM)

A filtration sequence as described in example 1 is then performed on the eluate in order to study the fibrinogen clogging profile on the 20 nm porosity nanofilter.

III—Results

The results are presented in the table below

| Elution buffer | Increasing concentrations of arginine added to the elution buffer | Nanofiltration capacity ($kg/m^2$) |
|---|---|---|
| Buffer pH 7.0 ± 0.2, 50 mM sodium citrate | 150 mM arginine HCL | 0.250 $kg/m^2$ |
| Buffer pH 7.0 ± 0.2, 50 mM sodium citrate | 200 mM arginine HCL | >0.350 $kg/m^2$ |
| Buffer pH 7.0 ± 0.2, 50 mM sodium citrate | 400 mM arginine HCL | >0.350 $kg/m^2$ |

Unexpectedly, a composition eluted chromatographically in buffer comprising increasing concentrations of arginine, without further addition of arginine prior to the nanofiltration step, allows an increase in the 20 nm nanofiltration capacity of fibrinogen.

Thus and advantageously, increasing concentrations of arginine in the elution buffer in accordance with the invention do not induce clogging of the filter and allow the nanofiltration capacity of the process to be increased, without the addition of arginine after the chromatographic purification step.

The invention claimed is:

1. A process for filtering a fibrinogen composition, comprising the following steps:
   a) chromatographic purification of the fibrinogen composition with an elution buffer comprising arginine;
   b) performing at least one filtraton step of the fibrinogen composition obtained by elution chromatography in step a) on a symmetrical filter having a pore size between 15 nm and 25 nm, and
   c) recovering the resulting fibrinogen solution,
   wherein the elution buffer used in step a) comprises an arginine concentration of at least 200 mM, and
   wherein the fibrinogen yield of the filtration is higher than 90% said filtration process being carried out without addition of arginine after step a).

2. The process of claim 1, further comprising at least one additional filtration step performed prior to the symmetrical filtration step, comprising filtering the fibrinogen on a filter having a pore size between 0.08μm and 0.22 μm.

3. The process of claim 1, further comprising at least one additional filtration step performed prior to the symmetrical filtration step, comprising filtering the fibrinogen comprising on a filter having a pore size between 0.08 um and 0.22 um; filtering the fibrinogen solution obtained in step b) on a filter having a pore diameter between 15 nm and 50 nm.

4. The process according to claim 2, wherein the symmetrical filter has a pore size between 18 nm and 22 nm.

5. The process according to claim 1, wherein the fibrinogen composition is obtained from plasma fractions, milk of transgenic animals, or cell culture supernatant.

6. The process according to claim 1, wherein the chromatographic purification step is performed by affinity, mixed-mode, or ion-exchange chromatography.

7. The process according to claim 1, wherein the elution buffer used in step a) comprises an arginine concentration between 200 mM and 800 mM.

8. The process according to claim 1, wherein the elution buffer used in step a) comprises an arginine concentration between 200 mM and 600 mM.

9. The process according to claim 1, wherein the elution buffer used in step a) comprises an arginine concentration between 200 mM and 400 mM.

10. The process according to claim 1, wherein the elution buffer used in step a) comprises an arginine concentration of at least 200 mM and said filtration process is carried out at a capacity of at least 0.25 kg/m$^2$.

11. The process according to claim 1, wherein the elution buffer used in step a) comprises an arginine concentration of at least 200 mM and said filtration process is carried out at a capacity of at least 0.35 kg/m$^2$.

12. The process according to claim 1, wherein the elution buffer used in step a) comprises an arginine concentration of at least 400 mM and said filtration process is carried out at a capacity of at least 0.25 kg/m$^2$.

13. The process according to claim 1, wherein the elution buffer used in step a) comprises an arginine concentration of at least 400 mM and said filtration process is carried out at a capacity of at least 0.35 kg/m$^2$.

14. The process of claim 1, further comprising at least one additional filtration step performed prior to the symmetrical filtration step, comprising filtering the fibrinogen on a filter having a pore size between 0.15 μm and 0.22 μm, and then filtering on a filter having a pore size between 0.08 μm and 0.15 μm.

15. The process according to claim 14, wherein the first filtration is carried out on a filter having a pore size of 0.2 μm, and the second filtration is carried out on a filter having a pore size of 0.1 μm.

16. The process according to claim 1, wherein said filtration process is being carried out without addition of arginine after step a), at a capacity of at least 0.2 kg fibrinogen/m$^2$, and said fibrinogen composition not being previously frozen and/or thawed.

* * * * *